(12) United States Patent
Amakawa

(10) Patent No.: US 6,894,192 B2
(45) Date of Patent: May 17, 2005

(54) PROCESS FOR PRODUCTION OF XYLYLENEDIAMINE

(75) Inventor: Kazuhiko Amakawa, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/643,981

(22) Filed: Aug. 20, 2003

(65) Prior Publication Data

US 2004/0039232 A1 Feb. 26, 2004

(30) Foreign Application Priority Data

Aug. 26, 2002 (JP) .......................... 2002-245222

(51) Int. Cl.$^7$ ...................... C07C 209/48; C07C 211/27
(52) U.S. Cl. ...................................... 564/415; 564/372
(58) Field of Search ................................ 564/372, 415

(56) References Cited

U.S. PATENT DOCUMENTS 4,482,741 A * 11/1984 Kurek .......................... 564/415
6,114,277 A    9/2000 Miura et al.

OTHER PUBLICATIONS

Database CAPLUS on STN, Acc. No. 2000:714722, Shen et al., Shanghai Huagong (2000), 25(17), p. 12–15 (abstract).*
Database CAPLUS on STN, Acc. No. 2000:739236, Shen et al., Jingxi Huagong (2000), 17(9), p. 544–546, 551 (abstract).*
Database CAPLUS on STN, Acc. No. 2000:43909, FR 2773086 (Jul. 2, 1999) (abstract).*
Database CAPLUS on STN, Acc. No. 1983:4292, EP 61042 (Sep. 29, 1982) (abstract).*
Database CAPLUS on STN, Acc. No. 1975:90651, AU 454487 (Oct. 16, 1974) (abstract).*
Database CAPLUS on STN, Acc. No. 1959:8487, GB 797111 (Jun. 25, 1958) (abstract).*
Database CAPLUS on STN, Acc. No. 1951:14652, GB 644239 (Oct. 4, 1950) (abstract).*
European Search Report mailed Dec. 12, 2003, for European Application No. EP 03 01 8532.
CAPLUS, 1999–666051, Lu, et al., Abstract of "Preparation of m–xylylenediamine with Raney Ni comprising iron and chromium".

* cited by examiner

*Primary Examiner*—Brian Davis
(74) *Attorney, Agent, or Firm*—Antonelli, Terry, Stout & Kraus, LLP

(57) ABSTRACT

In the process of the present invention for producing a xylylenediamine by a liquid-phase hydrogenation of a dicyanobenzene in the presence of a catalyst, the catalyst having its activity decreased during the course of use in the hydrogenation is reactivated and a pressure drop through a fixed bed catalyst layer is got rid of, thereby regenerating the catalyst for reuse in the subsequent hydrogenation of the dicyanobenzene to produce the xylylenediamine. The catalyst is regenerated by brought into contact with a hydrogen-containing gas under controlled temperature conditions.

14 Claims, No Drawings

PROCESS FOR PRODUCTION OF XYLYLENEDIAMINE

BACKGROUND OF THE INVENTION

1. Field of the Invention

The present invention relates to a process for producing a xylylenediamine by a liquid-phase hydrogenation of a dicyanobenzene in the presence of a catalyst, and more particularly, to a process for producing the xylylenediamine in which the catalyst having its activity decreased in the course of the hydrogenation is regenerated for reuse in the hydrogenation of the dicyanobenzene. The xylylenediamine is useful as a raw material for production of polyamide resins, curing agents, etc., as well as an intermediate material for isocyanate resins, etc.

2. Description of the Prior Art

It is well known in the art to produce the xylylenediamine by hydrogenating dicyanobenzene in the presence of a catalyst.

For example, Japanese Patent Publication No. 38-8719 discloses an autoclave batchwise hydrogenation of a dicyanobenzene into a corresponding diamine in an alcohol solvent in the presence of a very small amount of a caustic alkali agent and Raney nickel. Japanese Patent Application Laid-Open No. 54-41804 discloses another batchwise hydrogenation of a dicyanobenzene in an autoclave. The proposed hydrogenation is conducted in a mixed solvent of a lower alcohol and a cyclic hydrocarbon in the presence of a hydroxide or alcoholate of alkali metal or alkaline earth metal, and a Raney nickel catalyst to produce the corresponding diamine. Japanese Patent Publication No. 53-20969 discloses a catalytic reduction of a dicyanobenzene with hydrogen in a liquid phase in the presence of a Ni/Cu/Mo-containing catalyst, for example, by a fixed bed continuous hydrogenation.

However, in any of the above conventional methods, the catalyst is gradually deactivated during the course of use, resulting in unsatisfactory yields of the aimed product. In addition to such a lowering of the catalytic activity, in a fixed bed reactor, the pressure drop through the catalyst layer due to adhesion of high-boiling substances makes continuous operation of the reactor difficult.

Journal of Catalysis, 143 (1993), pp. 187–200 teaches that a nickel catalyst (25% by weight of nickel on $SiO_2$) used in a gas-phase hydrogenation of acetonitrile can be regenerated by a hydrogen treatment at 200° C. or higher.

Japanese Patent Application Laid-Open No. 2000-508305 teaches that a nickel-containing catalyst used for producing 6-aminocapronitrile and hexamethylenediamine simultaneously by hydrogenating adiponitrile can be regenerated by a hydrogen treatment at 150 to 400° C. under a hydrogen pressure of 0.1 to 30 MPa for 2 to 48 h.

Japanese Patent Application Laid-Open No. 2000-508304 discloses that a cobalt- or iron-containing catalyst used for producing an $NH_2$-containing compound by hydrogenating a compound containing a carbon-nitrogen unsaturated bond can be regenerated by a hydrogen treatment at 150 to 400° C. under a hydrogen pressure of 0.1 to 30 MPa for 2 to 48 h. This patent document teaches that aliphatic nitrites, especially adiponitrile is preferred as the compound containing a carbon-nitrogen unsaturated bond, and discloses the regeneration of the catalyst used in the hydrogenation of adiponitrile and 3-cyano-3,5,5-trimethylcyclohexylimine in its working examples.

Japanese Patent Application Laid-Open No. 2001-526956 discloses that a Raney nickel catalyst used for the hydrogenation of nitrites can be regenerated by treating the catalyst with an aqueous solution of a basic compound having a basic ion concentration of 0.01 mol/L or higher at a temperature of lower than 130° C., and then washed with water until the pH of the washings reaches 12 to 13, exemplifying the regeneration of the catalyst used for the hydrogenation of adiponitrile.

However, the above documents are all concerned with the regeneration of the catalysts used for the hydrogenation mainly of aliphatic nitrites, and silent as to whether or not catalysts used for the hydrogenation of aromatic dinitriles such as dicyanobenzene are equally regenerated by the proposed method, and also, whether or not a pressure drop through the catalyst layer of a fixed bed reactor can be got rid of by the proposed method.

SUMMARY OF THE INVENTION

An object of the present invention is to provide a process for producing a xylylenediamine by hydrogenating a dicyanobenzene in which a catalyst having its activity decreased during the course of the hydrogenation is regenerated for reuse in the subsequent hydrogenation of the dicyanobenzene.

Another object of the present invention is to provide a process for producing a xylylenediamine by hydrogenating a dicyanobenzene in which a pressure drop through a fixed bed catalyst layer generated during the course of the hydrogenation is got rid of for reuse in the subsequent hydrogenation of the dicyanobenzene.

As a result of extensive researches, the present inventors have found that the above object is achieved by treating the catalyst having its activity decreased or the catalyst layer generating a pressure drop in the presence of a hydrogen-containing gas under specific conditions. The present invention has been accomplished on the basis of this finding.

Thus, the present invention provides a process for producing a xylylenediamine by hydrogenating a dicyanobenzene in a liquid phase in the presence of a catalyst, the process comprising steps of bringing the catalyst having its activity decreased during the course of the hydrogenation of dicyanobenzene into contact with a hydrogen-containing gas at 200 to 500° C. while controlling a temperature rise speed of the catalyst to 40° C./min or less, thereby regenerating the catalyst; and a step of reusing the catalyst thus regenerated in the subsequent hydrogenation of the dicyanobenzene.

The present invention further provides a process for producing a xylylenediamine by hydrogenating a dicyanobenzene in a liquid phase in the presence of a catalyst, the process comprising a step of regenerating the catalyst having its activity decreased during the course of the hydrogenation of the dicyanobenzene by the following treatments (1) and (2):

(1) bringing the catalyst into contact with a hydrogen-containing gas at 140 to 200° C. for one hour or longer while controlling an average treating temperature to 180° C. or lower, and then (2) further bringing the catalyst thus treated into contact with a hydrogen-containing gas at 200 to 500° C.; and a step of reusing the catalyst thus regenerated in the subsequent hydrogenation of the dicyanobenzene.

DETAILED DESCRIPTION OF THE INVENTION

The present invention will be described in detail below.

The starting dicyanobenzene used in the present invention is a compound having two nitrile groups on the benzene ring, such as isophthalonitrile and terephthalonitrile. The benzene ring of the dicyanobenzene may also have, in addition to the two nitrile groups, another substituent, e.g., halogen atom such as fluorine and chlorine, alkyl group such as methyl and ethyl, and alkoxyl group such as methoxyl and ethoxyl. Examples of the substituted dicyanobenzenes include 2-chloroterephthalonitrile, 5-methylisophthalonitrile and 4-methylisophehalonitrile. These dicyanobenzenes are hydrogenated to the corresponding xylylenediamines.

In the present invention, the hydrogenation is conducted in a liquid phase, preferably using a solvent that is stable under the hydrogenation conditions. Examples of the solvent include hydrocarbons such as toluene, xylene and trimethylbenzene; ethers such as tetrahydrofuran and dioxane; lower aliphatic amides such as dimethylformamide and dimethylacetamide; alcohols such as methanol, ethanol and propanol; and ammonia. These solvents may be used singly or in combination of two or more. Since the yields of the xylylenediamine are increased in the presence of ammonia, ammonia is preferably used as a part of the solvent. The amount of the solvent is 1 to 99 parts by weight, preferably 1.5 to 99 parts by weight based on one part by weight of the dicyanobenzene.

The hydrogen gas used for the hydrogenation of the dicyanobenzene may contain impurities that take no part in the hydrogenation, such as methane and nitrogen. However, if the content of the impurities is too high, the total reaction pressure must be considerably increased to achieve a necessary hydrogen partial pressure, being industrially disadvantageous. The hydrogen concentration in the gas is preferably 50 mol % or higher.

In the process of the present invention, there may be used known hydrogenating catalysts such as supported metal catalysts, non-supported metal catalysts and Raney catalysts. Of these catalysts, preferred are those containing at least one catalytically active metal component selected from the group consisting of nickel, cobalt, palladium, ruthenium and rhodium, more preferred are nickel- and/or cobalt-containing catalysts, and most preferred are nickel-containing catalysts. As the carrier for the supported catalyst, there may be used alumina, silica, titania, zirconia or the like. If necessary, the catalyst may be modified by the addition of at least one element selected from the group consisting of Li, Na, K, Rb, Cs, Be, Ca, Ba, Ti, Cu, Cr, Zn, Mn, Mg, Fe, Ga, Ge, Nb, Ir, Pt, Bi, Al, Si, In, Sr, Ce and Mo.

In the present invention, an additive may be used to accelerate the hydrogenation or improve the yield. Examples of the additives include hydroxides or alcoholates of alkali metals or alkaline earth metals, such as lithium hydroxide, sodium hydroxide and potassium hydroxide.

The hydrogenation may be performed batch-wise or continuously either in fixed bed manner or in slurry bed manner, with a fixed bed continuous flow method being preferred because of its simplicity. The hydrogenation temperature is 20 to 250° C., preferably 20 to 200° C., and the hydrogenation pressure is 0.5 to 30 MPa, preferably 1 to 20 MPa. In a slurry bed hydrogenation, the catalyst is used preferably in an amount of 0.1 to 200 parts by weight base on 100 parts by weight of the starting dicyanobenzene. In a fixed bed hydrogenation, the starting dicyanobenzene is fed preferably in a rate of 0.01 to 1000 parts by weight/h based on 100 parts by weight of the catalyst.

In the present invention, to ensure a high yield of the xylylenediamine, the hydrogenation conditions such as temperature and feed rate of the raw material may be suitably selected such that the conversion of the dicyanobenzene is 95 mol % or higher, preferably substantially 100 mol %, and the yield of the intermediate cyanobenzylamine (e.g., 3-cyanobenzylamine when isophthalonitrile is used as the raw material) is 2 mol % or lower, preferably 1.0 mol % or lower. The intermediate cyanobenzylamine is generally difficult to be separated from the corresponding xylylenediamine by an ordinary distillation technique because of a small difference between the boiling points thereof. Therefore, to produce the xylylenediamine in high purity, the concentration of the cyanobenzylamine at the outlet of the hydrogenation system is preferably controlled to a low level, because the purification of the xylylenediamine becomes easy.

According to the present invention, the catalyst having its activity decreased during the course of use is regenerated by bringing the catalyst into contact with a hydrogen-containing gas. Prior to regenerating the catalyst, liquid components remaining in the reactor are removed. If desired, the catalyst may be washed with the solvent of the same type as used in the reaction. The used catalyst was separated and successively treated with a hydrogen-containing gas. The regeneration of the catalyst by the hydrogen-containing gas is preferably conducted in the same reactor as used for the hydrogenation of the dicyanobenzene because of simplicity.

The regeneration of the catalyst by the hydrogen-containing gas is performed at 200 to 500° C. When lower than 200° C., the effect of the regeneration is insufficient, while the catalyst may be deteriorated when higher than 500° C.

The temperature rise speed of the catalyst under contact with the hydrogen-containing gas in the regenerating treatment is controlled to 40° C./min or less (inclusive of zero), preferably 30° C./min or less, and more preferably 20° C./min or less. As will be described in detail below, the catalyst may be brought into contact with the hydrogen-containing gas at a temperature less than 200° C. prior to the regeneration treatment at 200 to 500° C. The temperature rise speed of the catalyst in such a pretreatment with the hydrogen-containing gas is also preferably controlled to 40° C./min or less (inclusive of zero). During the study on the regeneration of the catalyst by the hydrogen-containing gas, the inventors have found that the catalyst being regenerated changes its temperature differently according to its use history and the regeneration conditions, and that the catalyst temperature sometimes steeply rises to make the operation out of control. The inventors have further found that the steep rise of catalyst temperature during the regeneration reduces the performance of the catalyst after subjected to the regeneration treatment. As described above, the regeneration by the hydrogen-containing gas of the catalyst used in the hydrogenation of the dicyanobenzene is sometimes accompanied by the steep rise of catalyst temperature to make the operation out of control. Such a steep rise of catalyst temperature should be avoided because it is detrimental to a safe or stable operation and reduces the catalyst performance.

The inventors have found that the rise of catalyst temperature closely relates to the feed rate of hydrogen in the regeneration treatment. Therefore, the steep rise of catalyst temperature can be effectively avoided by controlling the feed rate of hydrogen in the regeneration treatment, i.e., by setting the feed rate of hydrogen to a low level. The feed rate of hydrogen is so controlled that the temperature rise of catalyst is 40° C./min or less while monitoring the catalyst temperature. The practical feed rate of hydrogen varies depending on the type of catalyst, the use history of catalyst, and the catalyst temperature, and is preferably 0.001 to 2000 NL/h (N: normal state of 0° C., 1 atm), more preferably 0.001 to 1000 NL/h per 1 kg of the catalyst.

The hydrogen-containing gas used for the regeneration of catalyst may contain inert impurities, such as methane and nitrogen, which do not adversely affect the regeneration of the catalyst. The hydrogen pressure in the regeneration is preferably 0.01 kPa to 30 MPa, more preferably 0.1 kPa to 15 MPa. If a lower hydrogen partial pressure, for example 0.1 MPa or lower, is intended, it is preferred to dilute hydrogen with an inert gas such as nitrogen because of its simplicity.

In the preferred embodiment of the present invention, the catalyst may be treated by the following step (1) prior to the generation treatment at 200 to 500° C. (step (2)). Namely, the regeneration of the catalyst may be conducted by the following two steps: (1) a step of bringing the catalyst into contact with a hydrogen-containing gas at 140 to 200° C. for one hour or longer while controlling an average treating temperature to 180° C. or lower (hereinafter referred to as "low-temperature step"), and (2) a step of further bringing the catalyst thus treated into contact with a hydrogen-containing gas at 200 to 500° C. (hereinafter referred to as "high-temperature step"). By the above two-step regeneration treatment, the catalyst can be more effectively regenerated. In addition, the two-step regeneration treatment can be preferably employed in the industrial-scale apparatus, because the generation of heat and gas by the regeneration treatment can be avoided.

The temperature for the low-temperature step is 140 to 200° C., and the average temperature thereof is 180° C. or lower. The average temperature referred to herein means an average temperature over a period of treating time of the low-temperature step in the range of 140 to 200° C., and is determined by dividing an integrated temperature with respect to the treating period of time by the treating period of time. During the low-temperature step, the treating temperature may vary within the range of 140 to 200° C., for example, the treating temperature may be controlled by any combination of keeping at constant, raising or lowering. The treating time of the low-temperature step is one hour or longer, preferably 1 to 20 h.

The high-temperature step is conducted at 200 to 500° C. The treating temperature of the high-temperature step may vary within the above range, for example, the treating temperature may be controlled by any combination of keeping at constant, raising or lowering. The treating time of the high-temperature step may be appropriately selected from the range of from 3 to 300 h. The treating time and the treating temperature varies depending upon the kind of catalyst being regenerated or the degree of deterioration in catalytic activity. If the catalyst is severely decreased in its activity, the treating time is preferably prolonged.

In the low-temperature step, the temperature rise speed of the catalyst under contact with the hydrogen-containing gas is controlled preferably to 40° C./min or less (inclusive of zero), more preferably to 30° C./min or less, and still more preferably to 20° C./min or less. If appropriate, the temperature rise speed of the catalyst in the high-temperature step may be also controlled to 40° C./min or less (inclusive of zero), more preferably to 30° C./min or less, and still more preferably to 20° C./min or less.

As described above, the rise of catalyst temperature closely relates to the feed rate of hydrogen in the regeneration treatment. The steep rise of catalyst temperature in the low-temperature step and the high-temperature step can be also effectively avoided by controlling the feed rate of hydrogen, i.e., by setting the feed rate of hydrogen to a low level. The feed rate of hydrogen is preferably so controlled that the temperature rise of catalyst is 40° C./min or less while monitoring the catalyst temperature. The practical feed rate of hydrogen varies depending on the type of catalyst, the use history of catalyst, and the catalyst temperature, and is preferably 0.001 to 2000 NL/h (N: normal state of 0° C., 1 atm), more preferably 0.001 to 1000 NL/h per 1 kg of the catalyst.

The hydrogen-containing gas used in the low-temperature step and the high-temperature step may contain inert impurities, such as methane and nitrogen, which do not adversely affect the regeneration of the catalyst. The hydrogen pressure in the low-temperature step and the high-temperature step is preferably 0.01 kPa to 30 MPa, more preferably 0.1 kPa to 15 MPa. If a lower hydrogen partial pressure, for example 0.1 MPa or lower, is intended, it is preferred to dilute hydrogen with an inert gas such as nitrogen because of its simplicity. The hydrogen-containing gases for the low-temperature step and the high-temperature step may be the same or different.

With the above treatments, the catalyst having its activity decreased during the course of the hydrogenation is regenerated, and the pressure drop through the fixed bed catalyst layer is got rid of, allowing the regenerated catalyst to be reused as the catalyst for hydrogenating the dicyanobenzene in the production of the xylylenediamine The present invention will be described in more detail by reference to the following examples. However, it should be noted that the following examples are only illustrative and not intended to limit the scope of the invention thereto.

EXAMPLE 1

Preparation of Catalyst

Into an aqueous solution prepared by dissolving 305.0 g of nickel nitrate hexahydrate ($Ni(NO_3)_2 \cdot 6H_2O$), 6.5 g of copper nitrate trihydrate ($Cu(NO_3)_2 \cdot 3H_2O$) and 7.1 g of chromium nitrate nonahydrate ($Cr(NO_3)_3 \cdot 9H_2O$) into 1 kg of pure water at 40° C., 29.6 g of diatomaceous earth was dispersed under stirring at 40° C. Then, an aqueous solution prepared by dissolving 128.6 g of sodium carbonate ($Na_2CO_3$) in 1 kg of pure water at 40° C. was poured into the resultant suspension under thorough stirring to prepare a precipitate slurry. After heated to 80° C. and held at that temperature for 30 min, the precipitate slurry was filtered to separate the precipitates, which were then washed with water, dried at 110° C. overnight, and then calcined in air at 380° C. for 18 h. The calcined powder was mixed with 3% by weight of graphite and made into 3.0 mm $\phi \times 2.5$ mm tablets by a tablet machine. The tablets were reduced at 400° C. under a hydrogen flow, and then, stabilized by an oxidation treatment overnight at a temperature from room temperature to 40° C. under a flow of diluted oxygen gas (oxygen/nitrogen=1/99 by volume). Then, the tablets were crushed and sieved to have a particle size of 12 to 28 mesh, thereby obtaining a catalyst A.

Hydrogenation Test

A tube reactor having an inner diameter of 10 mm was filled with 10 g of the catalyst A (packing height: 130 mm). The catalyst A was activated by reduction at 200° C. under hydrogen flow. Then, a hydrogenation raw material consisting of a mixed solution of isophthalonitrile (IPN), m-xylene (MX) and ammonia ($NH_3$) in a weight ratio of IPN:MX:$NH_3$=6:54:40 was introduced into the tube reactor from the top thereof at a feed rate of 32 g/h. The hydrogenation was allowed to proceed at 55° C. under a reaction pressure of 7 MPa by supplying hydrogen gas under pressure in a rate of 20 NL/h. The reaction solution sampled from the outlet of the reactor was analyzed by gas chromatography. The conversion of isophthalonitrile was 100%, the yield of m-xylylenediamine was 91.6 mol %, and the yield of 3-cyanobenzyldiamine was 0.1 mol %. The reaction was further continued by raising the temperature so as to maintain the above yields. After 24 days, the pressure difference between the inlet and the outlet of the catalyst layer was increased to 0.5 MPa, and the reaction was interrupted by stopping the supply of the hydrogenation raw material and hydrogen gas.

Regeneration of Catalyst

After cooling the catalyst layer to room temperature and returning the inner pressure of the reactor to atmospheric pressure, hydrogen was flowed through the catalyst layer at a rate of 5 NL/h. After heating the catalyst layer to 150° C., hydrogen was further allowed to continuously flow though the catalyst layer for 2 h (two-hour treatment at an average temperature of 150° C.). Thereafter, the temperature of the catalyst layer was raised to 260° C. at a rate of 4° C./min, and then, hydrogen was continuously flowed though the catalyst layer for 40 h. Finally, the catalyst layer was cooled to room temperature.

Hydrogenation Test after Regeneration

After regenerating the catalyst, the hydrogenation was performed again at 55° C. under the same conditions as described above. The conversion of isophthalonitrile was 100%, the yield of m-xylylenediamine was 90.9 mol %, and the yield of 3-cyanobenzylamine was 0.1 mol %, indicating that the regenerated catalyst was equivalent to the fresh catalyst in their catalytic activity. The pressure drop through the catalyst layer was 0.00 MPa, indicating that the pressure drop was completely got rid of.

COMPARATIVE EXAMPLE 1

Hydrogenation Test

A tube reactor having an inner diameter of 10 mm was filled with 10 g of the catalyst A (packing height: 130 mm). The catalyst A was activated by reduction at 200° C. under hydrogen flow. Then, a hydrogenation raw material consisting of a mixed solution of isophthalonitrile (IPN), m-xylene (MX) and ammonia ($NH_3$) in a weight ratio of IPN:MX:$NH_3$=6:54:40 was introduced into the tube reactor from the top thereof at a feed rate of 32 g/h. The hydrogenation was allowed to proceed at 55° C. under a reaction pressure of 7 MPa by supplying hydrogen gas under pressure in a rate of 20 NL/h. The reaction solution sampled from the outlet of the reactor was analyzed by gas chromatography. The conversion of isophthalonitrile was 100%, the yield of m-xylylenediamine was 90.9 mol %, and the yield of 3-cyanobenzyldiamine was 0.1 mol %. The reaction was further continued by raising the temperature so as to maintain the above yields. After 22 days, the pressure difference between the inlet and the outlet of the catalyst layer was increased to 0.5 MPa, and the reaction was interrupted by stopping the supply of the hydrogenation raw material and hydrogen gas.

Regeneration of Catalyst

After cooling the catalyst layer to room temperature and returning the inner pressure of the reactor to atmospheric pressure, hydrogen was flowed through the catalyst layer at a rate of 5 NL/h. After heating the catalyst layer to 150° C., hydrogen was further allowed to continuously flow though the catalyst layer for 2 h. Thereafter, the catalyst layer was cooled to room temperature.

Hydrogenation Test after Regeneration

After regenerating the catalyst, the hydrogenation was performed again at 55° C. under the same conditions as described above. The conversion of isophthalonitrile was 45.1%, the yield of m-xylylenediamine was 0.1 mol %, and the yield of 3-cyanobenzylamine was 28.6 mol %. The pressure drop through the catalyst layer was 0.4 MPa.

EXAMPLE 2

Hydrogenation Test

A tubular insulated reactor having an inner diameter of 0.4 m was filled with 0.9 t of a commercially available catalyst (Ni-3266E manufactured by Harshaw Co., Ltd.; nickel content: about 50%) to a packing height of 8 m. After activating the catalyst by reduction at 200° C. under a hydrogen flow, hydrogen gas and a hydrogenation raw material (IPN:MX:$NH_3$=6:21:73 by weight) each pre-heated to 55° C. were fed into the reactor from the top thereof at respective feed rates of 100 $Nm^3$/h and 1.5 t/h to allow the hydrogenation to proceed. The reaction pressure was 15 MPa. The reaction solution sampled from the outlet of the reactor was analyzed by gas chromatography. The conversion of isophthalonitrile was 100%, the yield of m-xylylenediamine was 92 mol %, and the yield of 3-cyanobenzyldiamine was 0.1 mol %. The reaction was further continued by raising the pre-heating temperature only of the raw material so as to maintain the yield of 3-cyanobenzyldiamine at 0.5 mol % or lower. After 28 days, the pressure difference between the inlet and the outlet of the catalyst layer was increased to 0.4 MPa, and the reaction was interrupted by stopping the supply of the hydrogenation raw material and hydrogen gas.

Regeneration of Catalyst

After cooling the catalyst layer to 45° C. and returning the inner pressure of the reactor to atmospheric pressure, nitrogen was flowed through the catalyst layer at a rate of 10 $Nm^3$/h. The temperature of nitrogen gas being fed was raised from room temperature to 140° C. over 3 h. While maintaining the feed of nitrogen gas, hydrogen gas was fed at a rate of 0.1 $Nm^3$/h. The temperature of the feed gas was raised to 200° C. over 2 h at a speed of 0.5° C./min. The average treating temperature during the temperature rise was 170° C. The temperature of the feed gas was successively raised to a final temperature of 340° C. over 6 h. While maintaining the feed gas at 340° C., the flow rate of hydrogen gas was increased stepwise to 3 $Nm^3$/h and the feed amount of nitrogen gas was reduced stepwise to zero. During the course of maintaining the catalyst between 200° C. and 340° C., hydrogen gas was fed for 15 h. The feeding of hydrogen gas was carried out by monitoring the catalyst temperature. No steep temperature rise over 10° C./min was observed throughout the regeneration treatment.

Hydrogenation Test after Regeneration

After regenerating the catalyst, the hydrogenation was performed again by feeding the raw material of 55° C. under the same conditions as described above. The conversion of isophthalonitrile was 100%, the yield of m-xylylenediamine was 91 mol %, and the yield of 3-cyanobenzylamine was 0.1 mol %, indicating that the regenerated catalyst was equivalent to the fresh catalyst in their catalytic activity. The pressure drop through the catalyst layer was 0.00 MPa, indicating that the pressure drop was completely got rid of.

COMPARATIVE EXAMPLE 2

Hydrogenation Test

A tubular insulated reactor having an inner diameter of 0.4 m was filled with 0.9 t of a commercially available catalyst (Ni-3266E manufactured by Harshaw Co., Ltd.; nickel content: about 50%) to a packing height of 8 m. After activating the catalyst by reduction at 200° C. under a hydrogen flow, hydrogen gas and a hydrogenation raw material (IPN:MX:$NH_3$=6:21:73 by weight) each pre-heated to 55° C. were fed into the reactor from the top thereof at respective feed rates of 100 $Nm^3$/h and 1.5 t/h to allow the hydrogenation to proceed. The reaction pressure was 15 MPa. The reaction solution sampled from the outlet of the reactor was analyzed by gas chromatography. The conversion of isophthalonitrile was 100%, the yield of m-xylylenediamine was 92 mol %, and the yield of 3-cyanobenzyldiamine was 0.1 mol %. The reaction was further continued by raising the pre-heating temperature only of the raw material so as to maintain the yield of 3-cyanobenzyldiamine at 0.5 mol % or lower. After 31 days, the pressure difference between the inlet and the outlet of the catalyst layer was increased to 0.4 MPa, and the reaction was interrupted by stopping the supply of the hydrogenation raw material and hydrogen gas.

Regeneration of Catalyst

After reducing the inner pressure of the reactor to atmospheric pressure, hydrogen gas per-heated to 280° C. was fed to the catalyst layer at a rate of 10 $Nm^3$/h. Immediately after beginning the feeding of hydrogen gas, a steep temperature rise occurred in the upper portion of the catalyst. The catalyst temperature was raised to 370° C. at highest to make the operation out of control. The temperature rise speed of the catalyst during the feed of hydrogen gas was 59° C. at highest. The feed of hydrogen gas was stopped and the catalyst layer was cooled to 140° C. by allowing nitrogen gas of room temperature to pass through the catalyst layer.

Then, nitrogen gas and hydrogen gas were fed again at respective rates of 10 Nm³/h and 0.1 Nm³/h. The temperature of the feed gas was raised to 340° C. at a speed of 0.5° C./min, and finally the feed of the hydrogen-containing gas was continued at 340° C. for 2 h. While maintaining the feed gas at 340° C., the flow rate of hydrogen gas was increased stepwise to 3 Nm³/h and the feed amount of nitrogen gas was reduced stepwise to zero. Thereafter, the feed of gas was continued for 5 h in total. The feeding of hydrogen gas was carried out by monitoring the catalyst temperature. No steep temperature rise over 10° C./min was observed throughout the repetitive treatment.

Hydrogenation Test after Regeneration

After regenerating the catalyst, the hydrogenation was performed again by feeding the raw material of 55° C. under the same conditions as described above. The conversion of isophthalonitrile was 100%, the yield of m-xylylenediamine was 82 mol %, and the yield of 3-cyanobenzylamine was 6 mol %, indicating the deterioration of the catalyst performance.

As seen from the examples, in the process of the present invention for producing the xylylenediamine by the hydrogenation of the dicyanobenzene, a catalyst having its activity decreased during the course of the reaction can be reactivated and the pressure drop through a fixed bed catalyst layer can be got rid of, thereby regenerating the catalyst for reuse in hydrogenating the dicyanobenzene to produce the xylylenediamine. In addition, in the process of the present invention, the catalyst can be safely and effectively regenerated because the steep rise of catalyst temperature that makes the apparatus out of control or deteriorates the catalyst performance can be avoided in the regeneration treatment by the hydrogen-containing gas. Therefore, the catalyst can be used repeatedly for a long period of time to extremely reduce the catalyst costs. Thus, the present invention is of great industrial value.

What is claimed is:

1. A process for producing a xylylenediamine by hydrogenating a dicyanobenzene in a liquid phase in the presence of a nickel and/or cobalt-containing catalyst, the process comprising a step of bringing the catalyst having its activity decreased during the course of the hydrogenation of dicyanobenzene into contact with a hydrogen-containing gas at 200 to 500° C. while maintaining the rise in catalyst temperature to 40° C./min or less, thereby regenerating the catalyst; and a step of reusing the catalyst thus regenerated in the subsequent hydrogenation of the dicyanobenzene.

2. The process according to claim 1, wherein a feed rate of hydrogen is regulated so as to maintain the rise in catalyst temperature at 40° C./min or less during contact with the hydrogen-containing gas.

3. The process according to claim 1, wherein the step for regenerating the catalyst comprises the following treatments (1) and (2):

(1) bringing the catalyst into contact with a hydrogen-containing gas at 140 to 200° C. for one hour or longer while maintaining an average temperature of 180° C. or less, and then (2) further bringing the catalyst thus treated into contact with a hydrogen-containing gas at 200 to 500° C.

4. The process according to claim 1, wherein the hydrogenation of dicyanobenzene is conducted in a fixed bed reactor.

5. The process according to claim 1, wherein the catalyst is a nickel-containing catalyst.

6. A process for producing a xylylenediamine by hydrogenating a dicyanobenzene in a liquid phase in the presence of a nickel and/or cobalt-containing catalyst, the process comprising a step of regenerating the catalyst having its activity decreased during the course of the hydrogenation of the dicyanobenzene by the following treatments (1) and (2):

(1) bringing the catalyst into contact with a hydrogen-containing gas at 140 to 200° C. for one hour or longer while maintaining an average temperature of 180° C. or less, and then (2) further bringing the catalyst thus treated into contact with a hydrogen-containing gas at 200 to 500° C. and a step of reusing the catalyst thus regenerated in the subsequent hydrogenation of the dicyanobenzene.

7. The process according to claim 6, wherein the step (1) is performed while maintaining the rise in temperature of the catalyst at 40° C./min or less.

8. The process according to claim 7, wherein the step (1) is performed while regulating a feed rate of the hydrogen-containing gas so as to maintain the rise in catalyst temperature at 40° C./min or less.

9. The process according to claim 8, wherein the step (1) is performed while feeding the hydrogen-containing gas at a rate of 0.001 to 1000 L/h (based on gas flow at standard conditions) per 1 kg of the catalyst.

10. The process according to claim 6, wherein the steps (1) and (2) are performed while maintaining the rise in catalyst temperature at 40° C./min or less.

11. The process according to claim 10, wherein the steps (1) and (2) are performed while regulating a feed rate of the hydrogen-containing gas so as to maintain the rise in catalyst temperature at 40° C./min or less.

12. The process according to claim 11, wherein the steps (1) and (2) are performed by feeding the hydrogen-containing gas at a rate of 0.001 to 1000 L/h (based on gas flow at standard conditions) per 1 kg of the catalyst.

13. The process according to claim 6, wherein the hydrogenation of dicyanobenzene is conducted in a fixed bed reactor.

14. The process according to claim 6, wherein the catalyst is a nickel-containing catalyst.

* * * * *